United States Patent [19]

Annati et al.

[11] Patent Number: 5,567,051
[45] Date of Patent: Oct. 22, 1996

[54] THERMAL TESTING OF CERAMIC COMPONENTS USING A THERMAL GRADIENT

[75] Inventors: Richard E. Annati, Phoenix; Allan J. Rodrigue, Chandler; James T. Sublett, Mesa; Craig W. Irwin, Tempe, all of Ariz.

[73] Assignee: AlliedSignal Inc., Morris Township, N.J.

[21] Appl. No.: 287,396

[22] Filed: Aug. 8, 1994

[51] Int. Cl.⁶ .............................. G01N 3/60; G01N 25/00
[52] U.S. Cl. ................................................ 374/57; 374/15
[58] Field of Search .................................. 374/57, 45, 4, 374/5, 15

[56] References Cited

U.S. PATENT DOCUMENTS

| | | | |
|---|---|---|---|
| 2,301,316 | 11/1942 | Orr et al. | 374/57 |
| 3,534,597 | 10/1970 | Webb | 374/57 |
| 4,559,824 | 12/1985 | Soma et al. | 374/57 |
| 4,592,662 | 6/1986 | Robbins et al. | 374/57 |

FOREIGN PATENT DOCUMENTS

| | | | |
|---|---|---|---|
| 0032984 | 3/1978 | Japan | 374/57 |
| 0118269 | 5/1987 | Japan | 374/57 |
| 3111440 | 5/1988 | Japan | 374/57 |
| 405107166 | 4/1993 | Japan | 374/57 |
| 406308007 | 11/1994 | Japan | 374/57 |
| 1486887 | 6/1989 | U.S.S.R. | 374/57 |

*Primary Examiner*—Diego F. F. Gutierrez
*Attorney, Agent, or Firm*—Jerry J. Holden; John R. Rafter

[57] ABSTRACT

Non-destructive evaluation of a ceramic nozzle is accomplished by generating a thermal gradient across the nozzle while it is mounted in a test rig. The thermal gradient is then measured and compared to a preselected gradient that is representative of the harshest condition to which the nozzle will be exposed during its operating life. The thermal gradient is adjusted until it approximates the preselected gradient. The nozzle is then observed for any cracks which reveal a weakness in the ceramic.

9 Claims, 2 Drawing Sheets

THERMAL TESTING OF CERAMIC COMPONENTS USING A THERMAL GRADIENT

GOVERNMENT RIGHTS

This invention was made with Government support under contract F33657-91-C-0006 awarded by the United States Air Force. The Government has certain rights in this invention.

TECHNICAL FIELD

The present invention relates to non-destructive evaluation methods, and in particular to such a method for ceramic components used in gas turbine engines.

BACKGROUND OF THE INVENTION

Microfocus X-ray inspection, fluorescent penetrant inspection and visual inspection are conventional, non-destructive evaluation techniques used on metal components before the component is mounted in a gas turbine engine. These techniques reveal flaws or cracks in the metal that would result in the component failing during its operating life. Thus, the component can be rejected before it is mounted in the engine. For a number of reasons, these techniques have not been very reliable when used on ceramic components. First, a ceramic component may have hidden cracks or flaws that are related to a weakness in the ceramic, but which cannot be detected due to resolution limitations of these techniques. Second, these techniques may detect flaws or cracks in the ceramic that are not indicative of weakness in relation to the anticipated operational stress for the part, resulting in the rejection of a perfectly good part.

Accordingly, there is a need for a non-destructive evaluation method for ceramic components that only detects flaws or cracks in the ceramic indicative of a weakness in relation to the anticipated operational stress that the material will be exposed to during engine operation.

SUMMARY OF THE INVENTION

An object of the present invention is to provide a non-destructive evaluation method for ceramic components that detects flaws or cracks in the ceramic indicative of a weakness in relation to the anticipated operational stress that the material will be exposed to during engine operation.

The present invention achieves this objective by providing a method in which a thermal gradient is generated across a ceramic component. The thermal gradient is then measured and compared to a preselected gradient representative of the largest thermal induced stresses the component will likely be exposed to during its operating life. The thermal gradient is adjusted until it approximates the preselected gradient. The ceramic component is then observed for any cracks which reveal a weakness in the ceramic.

DESCRIPTION OF THE PREFERRED EMBODIMENT

Figure 1:
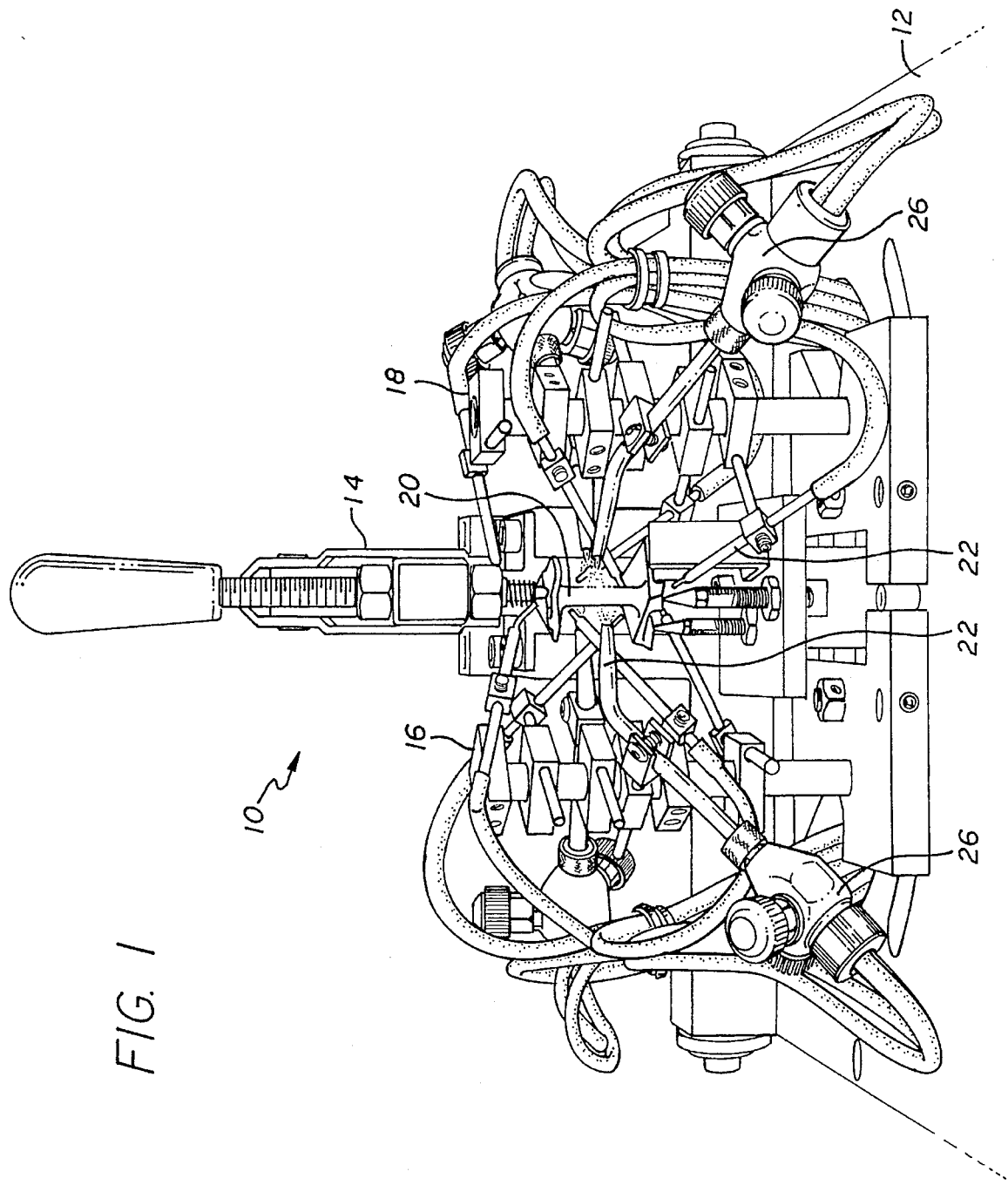
FIG. 1 shows a test rig used in the non-destructive evaluation method contemplated by the present invention.

Referring to FIG. 1, a test rig 10 is mounted on a table 12 and includes a holding fixture 14 disposed between two support posts 16, 18. The holding fixture 14 slides backwards, and the support posts 16, 18 swing apart. A ceramic turbine nozzle 20 is supported by the fixture 14. Mounted to the support posts 16, 18 are a plurality of impingement tubes 22. Some of the tubes 22, referred to as torches, deliver a jet of hot gas generated by igniting a mixture of oxygen and propylene. Alternatively, numerically controlled lasers can be used to apply heat. Other of the tubes 22 deliver cooling air. The flow of gas or air through each of the tubes 22 is controlled by a valve 26.

To calibrate the rig 10, the fixture 14 is positioned in its back position and the support posts 16, 18 are spaced apart. The torches are then lit, and the flow adjusted until the cone of each flame is about 3/16 inches long. The cooling air tubes are slightly opened to prevent the rig 10 from over heating. The nozzle 20 is mounted on the fixture 14 which is then moved forward. The posts 16, 18 are brought together so that the gas flows and air flows from the tubes 22 impinge on the surface of the nozzle 20. For the nozzle 20 two torches are directed at its leading edge and two at its trailing edge. Cooling air is directed to its fillet radii and to the outer surface of its inner and outer shrouds. After a few seconds exposure, the temperature distribution or gradient across the nozzle 20 stabilizes to steady state.

An optical fiber thermometer (OFT) is then used to measure this temperature gradient. The tip of the OFT is held as close to the nozzle surface as possible, preferably at a distance of about 0.025 inches to 0.05 inches. It is important to avoid touching the nozzle surface with the pyrometer as it will conduct energy away from the ceramic, locally cooling it. To ensure that the surface temperature of the nozzle 20 does not exceed 2200° F., measurements should first be made at the locations where the maximum temperatures are anticipated. A sufficient number of locations are measured so that a comparison can be made between the measured temperature gradient and a preselected temperature gradient.

Figure 2:
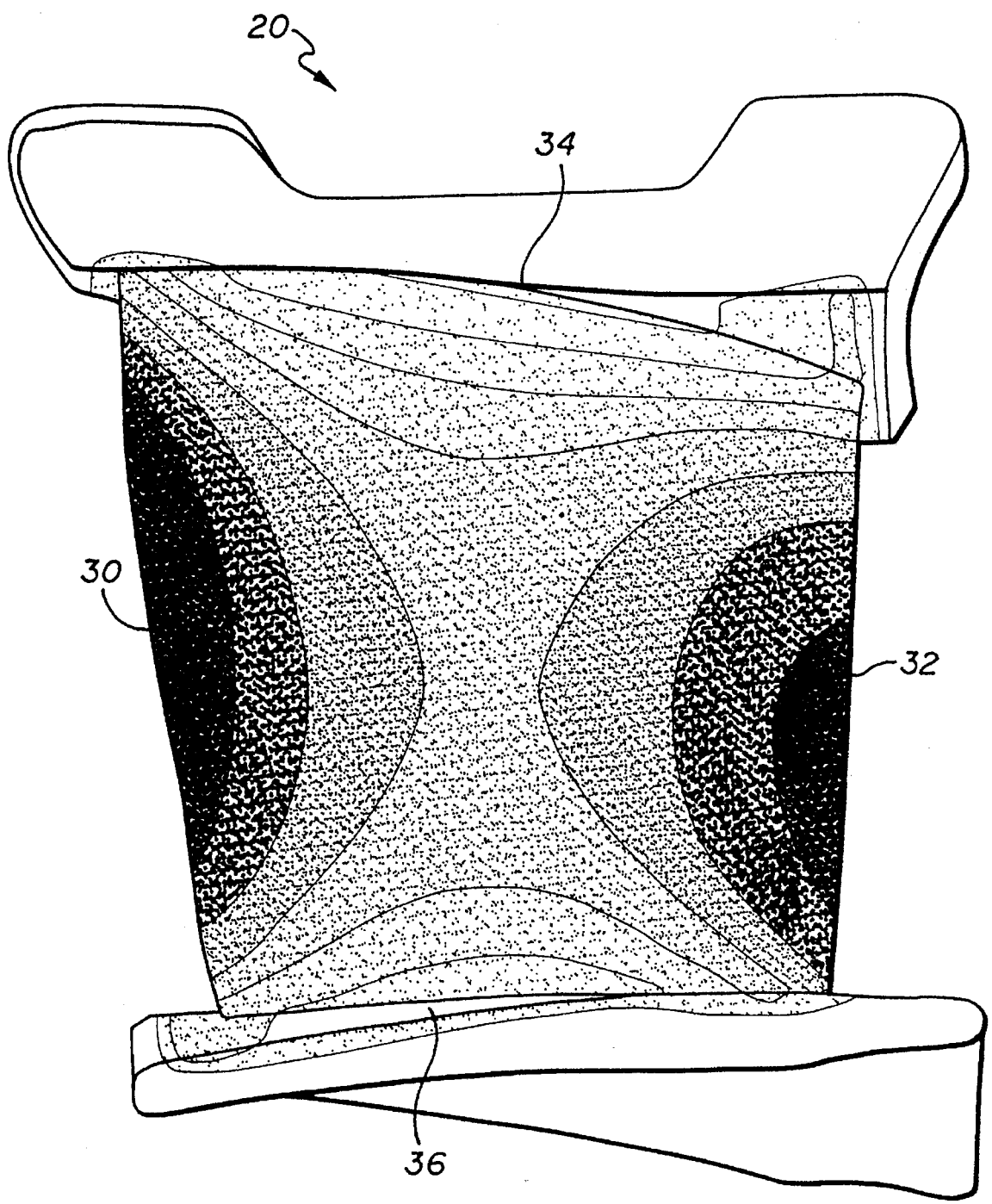
FIG. 2 is an illustration of a predetermined thermal gradient used in the non-destructive evaluation method contemplated by the present invention.

FIG. 2 shows a typical preselected temperature gradient for the gas turbine engine first turbine stage ceramic nozzle 20 in which regions of different temperature are highlighted by different colors, though FIG. 2 is in black and white with different shades representing different colors. For the nozzle 20 the highest temperatures occur at the leading and trailing edges 30, 32, and the coolest temperature at the outer and inner shrouds 34, 36. The preselected temperature distribution is generated by using computer models and represents the conditions under which the nozzle 20 will experience the largest thermally induced stresses during its operating life.

The flow of gas and air through the torches and cooling jets are adjusted until the measured temperature gradient agrees with the preselected gradient. In addition, the contours of the different temperature regions should also agree. This is easily checked as the nozzle 20 becomes translucent when heated.

With the impingement jets 22 calibrated to reproduce the preselected gradient, the posts 16, 18 are moved apart and the holding fixture 12 is moved backward. The rig 10 can now be used to test a plurality of nozzles one nozzle at a time. Each nozzle is mounted to the holding fixture 12, exposed to the jets 22 for about 10 seconds and observed. Cracks will appear on the surfaces of the nozzle, if there are any weakness related flaws in the ceramic.

Though the preferred embodiment has been described with reference to a ceramic nozzle used in a gas turbine engine. The subject invention is applicable to any ceramic component wherever it may be used.

Various modifications and alterations to the above described preferred embodiment will be apparent to those skilled in the art. Accordingly, this description of the invention should be considered exemplary and not as limiting the scope and spirit of the invention as set forth in the following claims.

What is claimed is:

1. A non-destructive evaluation method for a ceramic member comprising the steps of:

generating a thermal gradient across said ceramic member;

measuring said thermal gradient;

comparing said measured thermal gradient with a preselected thermal gradient;

adjusting said generating step until said measured thermal gradient is sufficiently like said preselected thermal gradient; and observing said ceramic member for any cracks.

2. The method of claim 1 wherein said generating step includes heating a first portion of said ceramic member.

3. The method of claim 2 wherein said heating step includes directing a flow of hot gas at said first portion.

4. The method of claim 2 wherein said generating step includes cooling a second portion of said ceramic member.

5. The method of claim 4 wherein said cooling step includes directing a flow of cooling air at said first portion.

6. The method of claim 1 wherein said ceramic member is a gas turbine engine nozzle.

7. A non-destructive evaluation method for a ceramic member comprising the steps of:

(a) exposing a first ceramic member to at least one impingement jet of hot gas and at least one impingement jet of cooling air;

(b) measuring a thermal gradient across said first ceramic member;

(c) comparing said measured thermal gradient with a preselected thermal gradient;

(d) adjusting the output of said impingement jets;

(e) repeating steps (b), (c), and (d) until said measured gradient is sufficiently like said preselected thermal gradient;

(f) replacing said first ceramic member with a second ceramic member;

(g) exposing said second ceramic member to said impingement jets; and observing said second ceramic member for any cracks.

8. The method of claim 7 wherein said preselected thermal gradient represents the conditions under which said second ceramic member will likely experience the largest thermal induced stresses during its operating life.

9. The method of claim 7 wherein step (g) lasts for about 10 seconds.

* * * * *